(12) United States Patent
Oku et al.

(10) Patent No.: US 6,320,067 B1
(45) Date of Patent: Nov. 20, 2001

(54) PROCESS FOR PRODUCING NITRILE

(75) Inventors: Masayuki Oku; Junji Koshino, both of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/579,436

(22) Filed: May 26, 2000

(30) Foreign Application Priority Data

Jun. 2, 1999 (JP) .................................................. 11-155729

(51) Int. Cl.⁷ .................................................. C07C 253/20
(52) U.S. Cl. .................................................. 558/314
(58) Field of Search .............................................. 558/314

(56) References Cited

U.S. PATENT DOCUMENTS

| 4,456,562 | 6/1984 | Tamura et al. . |
| 4,686,302 | 8/1987 | Merger et al. . |
| 5,349,103 | 9/1994 | Guelec . |
| 5,514,830 | * 5/1996 | Oku et al. .......................... 558/314 |
| 5,618,965 | 4/1997 | Kudschus . |

FOREIGN PATENT DOCUMENTS

| 0 550 762 | 7/1993 | (EP) . |
| WO 98/05630 | 2/1998 | (WO) . |

* cited by examiner

*Primary Examiner*—Floyd D. Higel
*Assistant Examiner*—Ebenezer Sackey
(74) *Attorney, Agent, or Firm*—Oblon, Spivak, McClelland, Maier & Neustadt, P.C.

(57) ABSTRACT

A nitrile having formula (2):

$$RC\equiv N \quad (2)$$

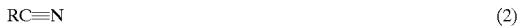

wherein R represents a substituted or unsubstituted alkyl, alkenyl, aralkyl or aryl group having 3 to 20 carbon atoms, is produced by a process, which comprises heating an aldoxime having formula (1):

$$RCH=NOH \quad (1)$$

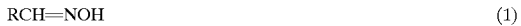

wherein R is as defined above, at 80 to 250° C. in the presence of a catalyst (A) of an alkali metal or alkaline earth metal salt of a saturated or unsaturated mono- or dicarboxylic acid having 2 to 20 carbon atoms while removing product water from the reaction system by distillation.

14 Claims, No Drawings

PROCESS FOR PRODUCING NITRILE

BACKGROUND OF THE INVENTION

1. Field of the Invention

The present invention relates to a convenient process for producing a nitrile which is useful as a perfume or as a raw material for the synthesis of perfumes, medicines, and the like in high yields.

2. Description of the Background

It is known that a nitrile can be prepared from a corresponding aldoxime by dehydration in the presence of a basic catalyst such as sodium hydroxide or potassium hydroxide (see WO 93/02046). According to this technique, an aldoxime is heated in the presence of the basic catalyst while product water is removed by distillation from the reaction system to give a nitrile in high yield. However, when this technique is applied to an aldoxime having a geometric isomer, such as 3,7-dimethyl-2,6-octadienoxime, the result is that the cis-trans ratio of the nitrile product is different from that of the raw oxime because of isomerization that has taken place during dehydration for unknown reasons, failing to provide a nitrile with the desired physical properties.

SUMMARY OF THE INVENTION

Accordingly, one object of the present invention is to provide a process of producing a nitrile, which achieves a high yield, suppresses isomerization that accompanies production of a nitrile having an alkenyl group, and is extremely advantageous from economic considerations in production.

Briefly, this object and other objects of the present invention as hereinafter will become more readily apparent can be attained by a process for producing a nitrile represented by formula (2):

$$RC\equiv N \quad (2)$$

wherein R represents a substituted or unsubstituted alkyl, alkenyl. aralkyl or aryl group having 3 to 20 carbon atoms, comprising heating an aldoxime represented by formula (1):

$$RCH=NOH \quad (1)$$

wherein R is as defined above, at 80 to 250° C. in the presence of an alkali metal or alkaline earth metal salt of a saturated or unsaturated mono- or dicarboxylic acid having 2 to 20 carbon atoms as a (dehydration) catalyst (hereinafter referred to as catalyst A) thereby distilling product water from the reaction system.

According to the invention, a nitrile can be produced in a high yield while suppressing isomerization that accompanies its formation where the nitrile has an alkenyl group. Therefore, the process of the invention is extremely advantageous from the standpoint of manufacturing economy.

DETAILED DESCRIPTION OF THE PREFERRED EMBODIMENTS

In formulae (1) and (2), the group represented by R contains 3 to 20 carbon atoms, preferably 6 to 14 carbon atoms. Suitable alkyl groups, as R, include heptyl, nonyl, undecyl, lauryl and myristyl. Suitable alkenyl groups, as R, include those having two or more double bonds such as 2,6-dimethyl-1,5-heptadienyl and 2,6-dimethyl-5-heptenyl. Suitable aralkyl groups, as R, include 2-phenethyl and 2-styryl. Suitable aryl groups, as R, include phenyl, methylphenvl and dimethylphenyl. Of these, R preferably represents an alkenyl group which provides a conjugated system in the resulting nitrile, such as 2,6-dimethyl-1,5-heptadienyl group or 2-styryl.

The group, as R, is preferably unsubstituted. However, the groups may be substituted with substituents which include cyano, hydroxyl, alkoxy, nitro, alkoxycarbonyl, amido, halogen and phenyl.

The aldoxime (1) raw material of the process of the present invention is obtained by, for example, reacting a corresponding aldehyde and an inorganic salt of hydroxylamine in a conventional manner.

Catalyst A employed in the present process, i.e., an alkali metal or alkaline earth metal salt of a saturated or unsaturated mono- or dicarboxylic acid having 9 to 20 carbon atoms, includes the sodium, potassium or magnesium salt of a monocarboxylic acid, such as acetic acid, propionic acid, stearic acid or oleic acid; and a sodium or potassium salt of a dicarboxylic acid, such as oxalic acid or maleic acid. Preferred salts include the alkali metal or alkaline earth metal salts of an aliphatic carboxylic acid. From economic considerations, an alkali metal salt of a lower fatty acid having 2 to 5 carbon atoms is preferred, with sodium acetate or potassium acetate being particularly preferred. These compounds can be used either individually or in a combination of two or more.

Catalyst A can be used in combination with another basic catalyst more basic than catalyst A, as long as the trans/cis ratio of the product nitrile is not adversely affected. The other basic catalyst that can be used in combination with catalyst A (hereinafter referred to as catalyst B) includes an alkali metal or alkaline earth metal hydroxide or an alkali metal or alkaline earth metal alkoxide having 1 to 6 carbon atoms, such as sodium hydroxide, potassium hydroxide, magnesium hydroxide, sodium methoxide or potassium methoxide. The molar ratio of catalysts B to A is preferably 3 or less, still preferably 2 or less, particularly preferably 1.0 or less. A preferred lower limit of the catalysts B to A molar ratio is 0.2.

In order to achieve an improved yield of the nitrile (2), catalyst A is preferably used or a combination of catalysts A and B in a total amount of 0.1 to 50% by weight, particularly 0.1 to 5% by weight, based on the aldoxime (1).

The reaction is conducted by heating the aldoxime at 80 to 250° C., preferably 80 to 200° C., still preferably 100 to 170° C. At temperatures below 80° C., the reaction rate is low for industrial production. At temperatures above 250° C., the nitrile decomposes to thereby causing a reduction in yield.

The means for removing water produced during the reaction by distillation is not particularly limited. For example, water can be driven out of the reaction system efficiently by azeotropic distillation using a solvent capable of forming a constant-boiling azeotrope with water or by vacuum distillation by decompression.

Solvents which form a constant-boiling azeotrope with water thereby enabling the removal of water from the system include benzene, toluene, xylene, chlorobenzene, heptane, methyl isobutyl ketone and ethyl acetate.

The vacuum distillation is preferably conducted by continuously removing the product water or product water with nitrile by distillation while continuously feeding the aldoxime (1) to a solution of the above-described catalysts in a high-boiling solvent under reduced pressure at the reaction temperature. The high-boiling solvent must have a higher boiling point than the product nitrile (2). Such solvents include liquid paraffin and alkylbenzenes.

The reaction by which the nitrile (2) is obtained from the aldoxime (1) is usually conducted under atmospheric pressure under which the product water is removed by azeotropic distillation using the azeotropic solvent or under reduced pressure of 27 kPa or less, particularly 8 kPa or less, where the product water is removed by vacuum distillation in the presence of the high boiling solvent. The resulting crude nitrile is purified by distillate on, column chromatography or a similar means to isolate the desired nitrile (2).

In the present invention, the cis-trans ratio of the unsaturated alkenyl group R changes very little from the raw aldoxime to the product nitrile. The rate of change in ratio (=((trans/cis ratio of raw oxime)−(trans/cis ratio of product nitrile))/(trans/cis ratio of raw oxime)) is preferably 0.10 or less.

The present invention will now be illustrated in greater detail with reference to Examples, but it should be understood that the invention is not construed as being limited thereto.

EXAMPLE 1

A flask was charged with 50 g of 3,7-dimethyl-6-octenoxime, 2 g of sodium acetate, and 25 ml of toluene, and the mixture was stirred at reflux at 126° C. for 2 hours while azeotropically distilling the product water together with toluene. After cooling to 30 to 40° C., the reaction mixture was neutralized with acetic acid, toluene was removed by evaporation, and the residue was distilled to give 44.0 g of a fraction (90° C./0.67 kPa). Analysis on the fraction revealed that 3.7-dimethyl-6-octenonitrile having a purity of 94.5% had been produced in a yield of 93.0% at a conversion of 99.0% and a selectivity of 94.0%. The conversion and the selectivity were calculated as follows.

Conversion (%)=((weight of charged oxime)−(weight of recovered oxime))/(weight of charged oxime)×100

Selectivity (%)=(mole number of produced nitrile)/(mole number of converted oxime)×100

EXAMPLE 2

A flask was charged with 30 g of liquid paraffin and 6 g of sodium acetate. The mixture was heated to 150° C. while stirring, and the inner pressure was reduced to 6.7 kPa. 3,7-Dimethyl-6-octenoxime was fed into the flask at a rate of 100 g/hr for 2 hours, followed by aging under the same conditions for 30 minutes. A 172 g amount of a nitrile fraction was obtained together with a small amount of water. Analysis on the fraction revealed the production of 3,7-dimethyl-6-octenonitrile with a purity of 93.5%, a yield of 90.0%, a conversion of 99.0%, and a selectivity of 91.0%.

EXAMPLE 3

A reaction was carried out in the same manner described in Example 2, except that sodium acetate was replaced with 4 g of potassium acetate. A nitrile fraction (170 g) was obtained together with a small amount of water. Analysis on the fraction revealed the production of 3,7-dimethyl-6-octenonitrile with a purity of 93.0%, a yield of 88.0%, a conversion of 99.0%, and a selectivity of 89.0%.

EXAMPLES 4 AND 5

A nitrite fraction was obtained in the same manner described in Example 1, except that the catalysts and the raw oximes shown in Table 1 below were used. The reaction results are also shown in the table.

TABLE 1

| Example | Raw Oxime | Catalyst | Produced Nitrile | Yield (%) | Conversion (%) | Selectivity (%) |
|---|---|---|---|---|---|---|
| 4 | 3-phenyl-propanoxime | potassium stearate | 3-phenyl-propanonitrile | 86 | 99 | 87 |
| 5 | 3-phenyl-2-propenoxime | potassium oxalate | 3-phenyl-2-propenonitrile | 79 | 99 | 80 |

EXAMPLE 6

Into a flask were placed 30 g of liquid paraffin and 4 g of potassium acetate. The mixture was heated to 150° C. while stirring, and the inner pressure was reduced to 6.7 kPa. 3,7-Dimethyl-2,6-octadienoxime having a trans/cis ratio of 1.2 was fed into the flask at a rate of 100 g/hr for 2 hours, followed by aging under the same conditions for 30 minutes. A 170 g amount of a nitrile fraction together with a small amount of water was obtained. Analysis on the fraction revealed that 3,7-dimethyl-2,6-octadienonitrile having a purity of 94.0% and a trans/cis ratio of 1.8 in a yield of 90.0% was obtained.

EXAMPLE 7

A nitrile fraction (177 g) was obtained together with a small amount of water in the same manner described in Example 6, except that 4 g of potassium acetate was replaced with 2.7 g of potassium acetate and 0.8 g of sodium hydroxide. Analysis on the fraction revealed the production of 3,7-dimethyl-2,6-octadienonitrile having a purity of 94% and a trans/cis ratio of 1.17 in a yield of 93%.

COMPARATIVE EXAMPLE 1

A nitrile fraction (170 g) was obtained together with a small amount of water in the same manner described in Example 6, except that potassium acetate was replaced with the same weight of sodium hydroxide. Analysis on the fraction revealed the production of 3, 7-dimethyl-2,6-octadienonitrile having a purity of 94.0% and a trans/cis ratio of 0.76 in a yield of 90.0%.

According to the process of the present invention, a nitrile can be produced in a high yield, by suppressing the isomerization that accompanies production of a nitrile having an alkenyl group, which is extremely advantageous from the viewpoint of economic considerations in production.

The disclosure of Japanese priority application Hei. 11-155729 filed Jun. 2, 1999 is hereby incorporated by reference into the present application.

While the invention has been described in detail and with reference to specific examples thereof, it will be apparent to one skilled in the art that various changes and modifications can be made therein without departing from the spirit and scope thereof.

What is claimed is as new and is intended to be secured by Letters Patent is:

1. A process for producing a nitrile having formula (2):

wherein R represents a substituted or unsubstituted alkyl, alkenyl, aralkyl or aryl group having 3 to 20 carbon atoms, which comprises:

heating an aldoxime having formula (1):

wherein R is as defined above, at 80 to 250° C. in the presence of a catalyst (A) of an alkali metal or alkaline earth metal salt of a saturated or unsaturated mono- or dicarboxylic acid having 2 to 20 carbon atoms while removing product water from the reaction system by distillation.

2. The process according to claim 1, wherein the amount of catalyst (A) ranges from 0.1 to 50% by weight based on the aldoxime.

3. The process according to claim 1, wherein the reaction at temperature is conducted in the presence of a catalyst (A) and another catalyst (B) which is more basic than catalyst (A).

4. The process according to claim 3, wherein the amounts of catalysts (A) and catalyst (B) total 0.1 to 50% by weight based on the amount of aldoxime.

5. The process according to claim 4, wherein the amounts of catalysts (A) and catalyst (B) total 0.1 to 5% by weight based on the amount of aldoxime.

6. The process according to claim 1, wherein R is heptyl, nonyl, undecyl, lauryl, myristyl, 2,6-dimethyl-1,5-heptadienyl, 2,6-dimethyl-5-heptenyl, 2-phenethyl, 2-styryl, phenyl, methylphenyl and dimethylphenyl.

7. The process according to claim 1, wherein R is an alkenyl group providing a conjugated system in the nitnile.

8. The process according to claim 6, wherein R is 2,6-dimethyl-1,5-heptadienyl or 2-styryl.

9. The process according to claim 1, wherein catalyst (A) is an alkali metal or alkaline earth metal salt of an aliphatic carboxylic acid or an aliphatic dicarboxylic acid.

10. The process according to claim 1, wherein catalyst (A) is sodium acetate or potassium acetate.

11. The process according to claim 3, wherein the molar ratio of catalyst (B) to catalyst (A) is 3 or less.

12. The process according to claim 3, wherein catalyst (B) is an alkali metal or alkaline earth metal hydroxide or an alkali metal or alkaline earth metal alkoxide having 1 to 6 carbon atoms.

13. The process according to claim 1, wherein the temperature of reaction ranges from 80 to 200° C.

14. The process according to claim 1, wherein said distillation is azeotropic distillation with added solvent selected from the group consisting of benzene, toluene, xylene, chlorobenzene, heptane, methyl isobutyl ketone and ethyl acetate.

* * * * *